United States Patent [19]

Mehra

[11] Patent Number: 4,883,514
[45] Date of Patent: * Nov. 28, 1989

[54] PROCESSING NITROGEN-RICH GASES WITH PHYSICAL SOLVENTS

[75] Inventor: Yuv R. Mehra, The Woodlands, Tex.

[73] Assignee: Advanced Extraction Technologies, Inc., Houston, Tex.

[*] Notice: The portion of the term of this patent subsequent to Nov. 18, 2003 has been disclaimed.

[21] Appl. No.: 74,226

[22] Filed: Jul. 16, 1987

Related U.S. Application Data

[63] Continuation-in-part of Ser. No. 24,561, Mar. 11, 1987, Pat. No. 4,740,222, which is a continuation-in-part of Ser. No. 854,383, Apr. 21, 1986, Pat. No. 4,743,282, which is a continuation-in-part of Ser. No. 828,996, Feb. 13, 1986, Pat. No. 4,696,688, and Ser. No. 828,988, Feb. 13, 1986, Pat. No. 4,680,042, each is a continuation-in-part of Ser. No. 808,463, Dec. 13, 1985, Pat. No. 4,642,174, which is a continuation-in-part of Ser. No. 784,566, Oct. 4, 1985, Pat. No. 4,817,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ .................................................. F25J 3/00
[52] U.S. Cl. ........................................... 62/17; 55/68; 55/75; 62/20
[58] Field of Search .................. 62/9, 11, 17, 18, 20; 55/68, 69, 74, 75

[56] References Cited

U.S. PATENT DOCUMENTS

| | | | |
|---|---|---|---|
| 1,934,029 | 11/1933 | Asbury | 23/210 |
| 2,183,604 | 12/1939 | Barton et al. | 196/8 |
| 2,204,042 | 6/1940 | Legatski | 62/175.5 |
| 2,237,386 | 4/1941 | Carney | 183/114.6 |
| 2,325,813 | 8/1943 | Throckmorton | 196/10 |
| 2,413,503 | 12/1946 | Katz | 196/8 |
| 2,428,521 | 10/1947 | Latchum, Jr. | 196/8 |
| 2,468,750 | 5/1949 | Gudenrath | 196/8 |
| 2,504,429 | 4/1950 | Latchum, Jr. | |
| 2,596,785 | 5/1952 | Nelly, Jr. et al. | 43/190 |
| 2,603,310 | 7/1952 | Gilmore | 183/115.6 |
| 2,663,169 | 12/1953 | Twomey | 62/175.5 |
| 2,716,332 | 8/1955 | Haynes | 62/123 |
| 2,744,394 | 5/1956 | Newton | 62/175.5 |
| 2,814,349 | 11/1957 | Koble | 183/115 |
| 2,857,018 | 10/1958 | Partridge et al. | 183/115 |
| 3,247,649 | 4/1966 | Miller | 55/40 |
| 3,555,837 | 1/1971 | McClintock | 62/17 |
| 4,158,556 | 6/1979 | Yearout | 62/17 X |
| 4,252,548 | 2/1981 | Markbreiter et al. | 62/17 |
| 4,318,723 | 3/1982 | Holmes et al. | 62/20 |
| 4,370,156 | 1/1983 | Goddin, Jr. et al. | 62/17 |
| 4,401,450 | 8/1983 | Schramm | 62/13 |
| 4,479,871 | 10/1984 | Pahade et al. | 208/340 |
| 4,588,427 | 5/1986 | Yao et al. | 62/17 |
| 4,623,371 | 11/1986 | Mehra | 62/17 |

OTHER PUBLICATIONS

"Gas Conditioning," under Natural Gas in vol. 11 of *Kirk-Othmer Encyclopedia of Chemical Technology*, Third Edition, 1980, pp. 638–641.

"Absorption" under Liquefied Petroleum Gas in vol. 14 of *Kirk-Othmer Encyclopedia of Chemical Technology*, Third Edition, 1980, pp. 383–388.

*Primary Examiner*—Ronald C. Capossela
*Attorney, Agent, or Firm*—Depaoli & O'Brien

[57] ABSTRACT

A process is described for processing an inert-rich natural gas stream with a lean oil physical solvent to obtain a specification-grade inert gas product, and a specification-grade hydrocarbon gas product, preferably in combination with an existing absorber plant. The process is an adaptation of the extractive flashing and extractive stripping versions of the Mehra Process.

5 Claims, 3 Drawing Sheets

PROCESSING NITROGEN-RICH GASES WITH PHYSICAL SOLVENTS

RELATED APPLICATIONS

This is a continuation-in-part of copending application Ser. No. 024,561, filed Mar. 11, 1987, now U.S. Pat. No. 4,740,222, entitled "RECOVERY AND PURIFICATION OF HYDROGEN FROM REFINERY AND PETROCHEMICAL OFF-GAS STREAMS", which is a continuation-in-part of co-pending application Ser. No. 854,383, filed Apr. 21, 1986, now U.S. Pat. No. 4,743,282, which is a continuation-in-part of co-pending application Ser. No. 828,996, filed Feb. 13, 1986, now U.S. Pat. No. 4,696,688, and of co-pending application Ser. No. 828,988, filed Feb. 13, 1986 and now U.S. Pat. No. 4,680,042, which are continuations-in-part of co-pending application Ser. No. 808,463, filed Dec. 13, 1985, now U.S. Pat. No. 4,692,179, which is a continuation-in-part of co-pending application Ser. No. 784,566, filed Oct. 4, 1985, now U.S. Pat. No. 4,817,038, which is a continuation-in-part of co-pending application Ser. No. 759,327, filed July 26, 1985, now U.S. Pat. No. 4,623,371, which is a continuation-in-part of co-pending application Ser. No. 758,351, filed July 24, 1985, now U.S. Pat. No. 4,601,738, which is a continuation-in-part of co-pending application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to removing and recovering methane and higher boiling hydrocarbons from a natural gas stream which contains large quantities of inert gases, may contain acidic components such as $CO_2$ and $H_2S$, and may vary in moisture content from dry to saturated. It specifically relates to the upgrading of heating values of natural gas streams having heating values below desired specifications. It further relates to adapting the extractive flashing and extractive stripping versions of the Mehra Process for processing of nitrogen-rich natural gas streams.

2. Review of the Prior Art

Many hydrocarbon gases, such as natural gas, are contaminated with one or more inert gases which lower their heat content or otherwise impair their marketability. Such inert gases include nitrogen, helium, and argon.

During recent years, there has been strong emphasis on the secondary and tertiary methods of recovering oil from formations where the primary oil-producing methods are no longer productive. Nitrogen injection for reviving these oil wells is not useful in most formations, but in some formations such as in the central and north Texas areas of the United States, nitrogen injection has been successfully utilized for the recovery of additional oil.

After several years of nitrogen injections at high pressure, approximately 14,000 Kpa (2,030 psia), the nitrogen seems to have broken through the formations in many instances. In other words, nitrogen is coming out with the oil, and it is separated from the oil at the separator. Previously, the associated gases were rich in hydrocarbons heavier than methane, along with substantial quantities of methane. The present dilution effect of nitrogen has caused the same associated wellhead gas to have an extremely low heat content, thereby making it unsuitable for pipeline shipments. If the natural gas contains more than 3% of nitrogen, it is off-specification for most of the world's pipelines.

This situation has caused the oil producer to curtail oil production because government regulations prevent him from burning the nitrogen-rich associated gas, and both environmental laws and a desire to preserve valuable resources prohibit him from venting the associated hydrocarbons. The oil producer is thus limited by the choice of technology available to him for properly processing the associated gases from an oil well. The prior art technology, which involves cryogenic principles, cannot economically process the natural gas streams which contain more than 3% nitrogen even after subsidization with the revenues from oil production.

Natural gas is a mixture of hydrocarbons, including methane, ethane, propane, and various amounts of higher molecular weight hydrocarbons together with nitrogen and acid gases, such as $CO_2$ and/or $H_2S$. A "dry" gas is one containing predominantly methane with some ethane, propane, and butane and having a very low hydrocarbon dew point. The heavier the hydrocarbons, such as pentane and higher homologs, that are present in the gas, the higher the hydrocarbon dew point. For pipeline transmission, enough of the heavier hydrocarbons must be removed to lower the dew point without losing too many of the calories needed to meet specifications. In the past, gases with large quantities of high molecular weight hydrocarbons have been passed through gasoline extraction plants and/or dew point control stations to lower the dew point. Also, frequently the gas has required conditioning to remove sulfur compounds and carbon dioxide.

Inability to change the composition of this liquid in accordance with market conditions has often been a handicap. The extractive flashing version of the Mehra Process, as described in U.S. Pat. Nos. 4,421,535, 4,511,381, 4,526,594, and 4,578,094, and the extractive stripping version of the Mehra Process, as described in U.S. Pat. Nos. 4,617,038, 4,692,179 have provided a solution for this problem with respect to recovering $C_2+$ hydrocarbons.

In addition, an improved extractive flashing version and an improved extractive stripping version of the Mehra Process are respectively described in U.S. Pat. Nos. 4,623,371 and 4,680,042 for separating $C_2+$ hydrocarbons from a nitrogen-rich hydrocarbon gas containing from 3 to 75 mol % nitrogen, the remainder being hydrocarbons. U.S. Pat. Nos. 4,623,371 and 4,680,042 are incorporated herein by reference.

These patents disclose processes capable of removing an inert gas from an inert-rich natural gas stream by oil producers who have been using nitrogen injection and by natural gas producers whose wells contain nitrogen, helium, and/or argon. In addition, these processes produce an acceptable hydrocarbon gas product and a natural gas liquids product from an inert-rich hydrocarbon gas stream and selectively adjust the heat content of the gas product and the hydrocarbon contents of the liquids product in accordance with market economics, thereby enabling the operator of a natural gas liquids extraction plant to minimize ethane recovery and maximize propane recovery, for example, in response to market conditions, while also producing an $N_2$-rich gas product.

In areas where the natural gas contains more than 3 mol % of nitrogen, helium, and/or other inert gases, there are many absorber plants utilizing lean oils as the solvent for recovering $C_2+$ hydrocarbons as the natural gas liquids (NGL) product. Because of the nitrogen content of the residue gas, it is often out of limits as a sales gas. These plants may be operating under borderline economic conditions and for economic reasons need a method for continuing operation while utilizing the same solvent. Lean oils which are customarily circulated in such absorber plants are low in selectivity capability for hydrocarbons, generally having a relative volatility of methane over ethane that is less than 5.0 and a hydrocarbon loading capacity, defined as solubility of ethane in the lean oils, of less than 3.5–34 normal cubic meters of ethane per cubic meter (0.49–4.8 standard cubic feet of ethane per gallon) of solvent.

SUMMARY OF THE INVENTION

It is accordingly an object of this invention to provide a process for treating an inert-rich natural gas stream that operates in combination with an existing lean oil absorber plant to separate the methane and the inert gas from the $C_2+$ hydrocarbon gases and then to recover specification-grade methane from the inert gas/methane mixture.

A further object is to provide a process for treating a natural gas stream that is rich in one or more inert gases by utilizing a lean oil or a mixture thereof as the solvent for extracting ethane and heavier hydrocarbons from both methane and the inert gas and then for extracting methane from the inert gas, thereby forming three separate product streams.

It is another object to provide a process for treating an inert-rich natural gas stream with lean oils as the physical solvent in order to upgrade the specific heat value thereof.

It is also an object to recover desired hydrocarbon gas liquids from nitrogen-rich gas streams at minimum capital cost and minimum operating expense while simultaneously producing specification grades of methane and nitrogen product streams.

These objectives are achieved, according to the principles of this invention, with a continuous process for treating an inert-rich natural gas stream containing more than 3 mole percent of an inert gas by contacting the gas stream with a stream of lean oils as the physical solvent to produce a mixture of methane and inert gas and then by contacting this mixture with the same lean oils to produce a nitrogen-rich overhead stream and a rich solvent stream which is flashed to produce a methane-rich hydrocarbon gas product meeting desired inert-gas specifications. The contacting is at a solvent flow rate which is selectively varied from 0.1 to 70 cubic meters (0.001 to 0.5 gallon per standard cubic foot) of solvent per thousand normal cubic meters of the natural gas stream. The solvent is selective toward ethane and heavier hydrocarbon components of the natural gas stream over methane such that:

(1) the relative volatility of methane over ethane is at least 1.0 and the hydrocarbon loading capacity of the solvent, defined as solubility of ethane in solvent, is at least 2.0 normal cubic meters of ethane per cubic meter (0.28 standard cubic foot of ethane per gallon) of solvent, or (2) its preferential factor, which is determined by the multiplication of relative volatility of methane over ethane by the solubility of ethane in the solvent, in normal cubic meters of ethane per cubic meter of solvent, is at least 2.0 (0.28 standard cubic foot of ethane per gallon of solvent). The inert gas in the inert-rich natural gas stream is nitrogen, helium, and/or argon, or mixtures thereof, the remainder being hydrocarbons. The inert-rich natural gas stream can also be sweet or sour, wet or dry. This process is also operable at the wellhead, whereby the natural gas product is suitable for pipeline shipment.

The contacting of the inert-rich natural gas stream with the physical solvent stream is at 500–9,100 Kpa absolute (72.5–1,320 psia). The flow rate of the physical solvent stream is selectively adjusted to produce the $C_1$-rich gas product meeting pipeline specifications for inert-gas content.

The inert-rich natural gas stream is selected from the group consisting of

A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

When the process of this invention is to be constructed in a natural gas supply area without being combined with an existing lean oil plant, i.e., as an independent installation, the methane extraction column may include a reboiler so that it is operable in extractive stripping (ES) mode, as disclosed in U.S. Pat. No. 4,617,038, except that the column is provided with an additional stage to remove the $C_1$ and with both a flashed solvent slipstream to the midsection of the column and a regenerated (lean-and-dry) solvent stream to the top of the additional stage. Such an independent installation may be characterized as an extractive stripping/flashing (ES/F) version of the invention.

Although the absorber and the methane extractor are generally simple absorber columns, as in typical lean oil plants, they may be equipped with bottom and/or side reboilers and/or side coolers. If operated with lean oils having the lowest possible preferential factor, they are truly operating as absorbers, but if aromatic or cyclo hydrocarbons are substituted to any significant degree for the paraffinic lean oil, they are operable as extractors in the same sense as in U.S. Pat. Nos. 4,617,038 and 4,680,042 and other patents describing the Mehra Process.

The recycle solvent stream that is produced by flashing is split according to one embodiment into a main solvent stream, containing less than 15 mole percent hydrocarbons, and a solvent slipstream which is regenerated to form a lean-and-dry solvent stream, which is lean with respect to $C_1+$ hydrocarbons and dry with respect to water, for recycling to the extracting step. The lean-and-dry solvent stream contains less than 1 wt. % of water (equivalent to less than 118 kg of water per million normal cubic meters (6,910 lbs. of water per million standard cubic feet) in the residue natural gas stream) and less than 1 volume % of $C_5+$ hydrocarbons.

The inert gas is then injected into the ground, vented to the atmosphere, or utilized for any other purpose.

The methane-rich solvent is flashed to a significantly lower pressure, sufficiently lower to release the methane and any other heavier hydrocarbons from the solvent. The solvent may then be sent to the regeneration operation, in whole or in part, or may be re-used, because of its dryness and leanness, for the extraction of the methane from the $C_1/N_2$ in the second stage of the methane extractor column.

In contrast to extractive flashing, extractive stripping may or may not utilize a flashing step for separating $C_1$-rich gases from the rich solvent. Separating $C_1+$ hydrocarbons from the inert gas product by total hydrocarbon extraction requires no more than one extractive stripping (ES) column and a hydrocarbon product (HP) column, but separating the hydrocarbon gas product (generally, as the $C_1$-rich product) from the $C_2+$ hydrocarbons, as hydrocarbon liquids product, requires an additional extractive stripping column which must be preceded by a solvent regenerating column. In this invention, however, the $C_1+$ gas product produced by flashing is to be considered as fuel for burning that meets pipeline specifications or as raw material for selective treatment according to the Mehra Process in order to remove $C_2+$ hydrocarbons.

The operating pressure and the temperature conditions of the ES/F column in a new installation can vary from 500 to 9,100 Kpa absolute (72.5 to 1,320 psia) and $-40°$ C. to $320°$ C. ($-40°$ to $608°$ F.), respectively.

Combined preferential factors are given in the following Table I for a common lean oil, NMP, DMF, and mesitylene.

Typical paraffinic lean oils, as given in the Table, are straddled by NMP and DMF at one extreme and by aromatic lean oils, as exemplified by mesitylene as an outstanding example, at the other. It is thus evident that lean oils vary considerably as to preferential factor, particularly because of variations in loading capacity (i.e., solubility). Moreover, the paraffinic lean oils, as indicated by the range given in the Table, have a fairly substantial variation of their own, but the best of them have preferential factors that are slightly below that of DMPEG (dimethyl ether of polyethylene glycol) and have consequently been classified as too low to be economically selective for the purpose of treating gas streams and selectively recovering the $C_2+$ hydrocarbons, as disclosed in U.S. Pat. No. 4,511,381 and subsequent Mehra patents.

Nevertheless, physical solvents having preferential factors in the lean oil range are suitable for separating methane from nitrogen, as disclosed in U.S. Pat. Nos. 4,623,371 and 4,680,042. If selective recovery of the $C_2+$ hydrocarbons is not a needed capability, moreover, even the paraffinic lean oils are useful for this purpose even though they also tend to absorb more nitrogen than a physical solvent having a higher preferential factor. The lower the preferential factor of a selected physical solvent, however, the more methane recovery must be sacrificed in order to attain a desired methane quality. In other words, recovery must generally be sacrificed, for purity because methane, as sales gas, must contain no more $N_2$ than permitted by pipeline specifications.

TABLE I

Preferential Factors Defining Preferential Physical Solvents for Mehra Process Applications

| SOLVENT | NMP | DMF | LEAN OIL | DMPEG | MESITYLENE |
|---|---|---|---|---|---|
| Relative volatility ($\alpha$) | 5.3 | 8.5 | 2.5–4.8 | 6.4 | 6.9 |
| Solubility, $Nm^3/m^3, \gamma$ | 0.2 (0.03) | 0.28 (0.04) | 1.4–7.0 (0.20–0.99) | 7.0 (0.99) | 29.7 (4.20) |
| Preferential factor ($\alpha \times \gamma$) | 1.1 (0.16) | 2.4 (0.34) | 3.5–34 (0.49–4.8) | 45 (6.4) | 205 (29.0) |

Physical solvents include all compounds which absorb others without a chemical reaction. For example, even water is a physical solvent for methane though a very poor one. Solvents may be characterized as to: (1) relative volatility for a selected solute as compared to another solute and (2) loading capacity for the selected solute and similar solutes. As defined herein and in U.S. Pat. No. 4,617,038, for example, the product obtained by multiplying relative volatility by loading capacity is defined as the preferential factor for a physical solvent.

Lean oils range in preferential factor from about 2.0 to at least about 10 normal $m^3$ (0.28 to at least about 1.4 standard cubic feet of solute gas per gallon of the solvent) of solute gas per $m^3$ of solvent. Some hydrocarbon solvents having some degree of preferential capability, as shown in the Table, have good relative volatilities but very poor solubilities (i.e., loading capacities for hydrocarbons). NMP, N-methyl pyrollidone, and DMF, dimethyl formamide, are suitable examples of such solvents, having respective preferential factors of 1.1 (0.16) and 2.4 (3.4).

To avoid such lowered recovery, a physical solvent having a high preferential factor may be partially admixed with a physical solvent, such as common or paraffinic lean oils typically used in natural gas processing plants for the recovery of $C_2+$ hydrocarbons, having a low preferential factor. Such admixture should be made on an economic basis by balancing the cost of lowered methane recovery against the additional cost of a physical solvent having a sufficiently high preferential factor.

Suitable lean oils include paraffinic, aromatic, and cyclo hydrocarbons and mixtures thereof in any proportion and having an average molecular weight of 75–250. Suitable aromatic hydrocarbons are rich in $C_8$–$C_{10}$ aromatic compounds having methyl, ethyl, or propyl aliphatic groups and specifically constituting a sub-group consisting of mesitylene, n-propyl benzene, n-butyl benzene, cumene, o-xylene, m-xylene, p-xylene, and mixtures thereof, and aromatic streams rich in mixed xylenes, $C_9$ alkylaromatics, and other $C_8$–$C_{10}$ aromatics, rich being defined with respect to the solvent as more than 15% by weight of the aromatic compound.

These compounds boil in the range of 130°–220° C. (266°–428° F.).

DESCRIPTION OF THE PREFERRED EMBODIMENTS

Figure 1:
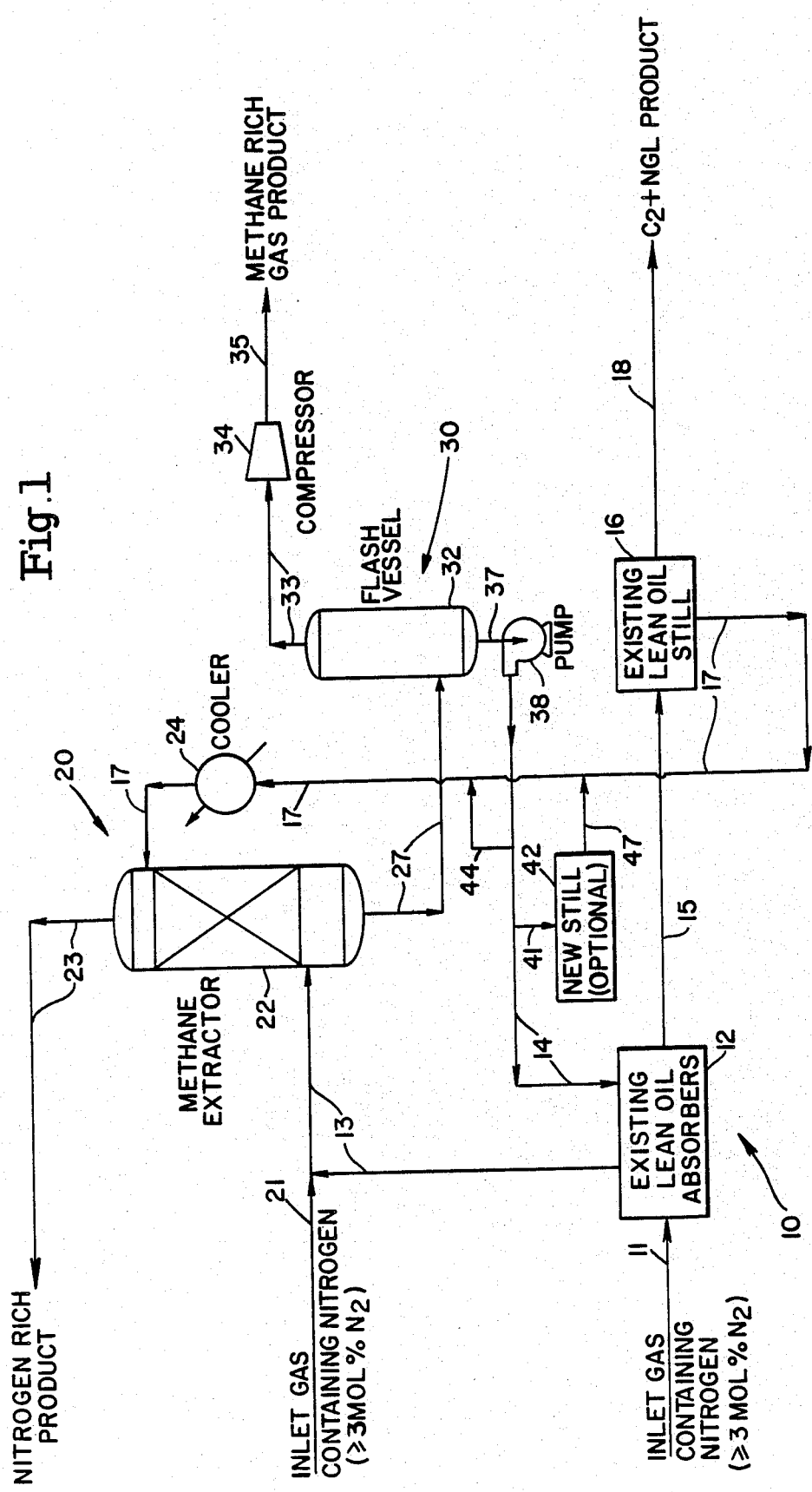
FIG. 1 is a schematic flow sheet illustrating the principal units of a conventional lean oil absorber process, shown as block diagrams, and the added units of this invention wherein all of the lean oil is regenerated.

With reference to the figures, it should be understood that pipelines are in fact being designated when streams are identified hereinafter and that streams are intended, if not stated, when materials are mentioned. Moreover, flow-control valves, temperature regulatory devices, pumps, and the like are to be understood as installed and operating in conventional relationships to the major items of equipment which are shown in the drawings and discussed hereinafter with reference to the continuously operating process of this invention. All of these valves, devices, and pumps, as well as heat exchangers, accumulators, condensers, and the like, are included in the term, "auxiliary equipment".

The process shown schematically in FIG. 1 comprises an existing lean oil absorber plant 10, a methane extractor unit 20, and a flash unit 30. Plant 10 typically comprises a plurality of existing lean oil absorbers 12 and an existing lean oil still or distillation column 16.

Methane extractor unit 20 comprises a methane extractor column 22 and a cooler 24. Flash unit 30 comprises a flash vessel 32, a compressor 34, and a solvent pump 38.

Inlet gas containing at least 3 mol % nitrogen is fed to absorber's 12 through line 11 while a stream of lean oil is fed thereto through line 17 from the bottom of still 16. Absorbers 12 produce an overhead stream 13 of methane and nitrogen and a rich solvent stream 15 which is fed to still 16. This still 16 produces an overhead product stream 18 of $C_2+$ NGL product and a regenerated stream 17 of lean oil which is typically recycled to absorber 12.

If operated with conventional lean oil solvent, plant 10 will perform in its customary manner, but if this lean oil is partially or entirely replaced with aromatic or cyclo lean oils, the lean oil flow rate may be significantly reduced while achieving the same results.

The process of this invention operates when $C_1/N_2$ stream 13 and regenerated solvent stream 17, after it has passed through oil cooler 24, are fed to methane extractor 22. These streams are in countercurrent contact within extractor 22 and leave as overhead nitrogen-rich stream 23 and rich solvent stream 27 which is fed to flash vessel 32 in which pressure is reduced. The flashed gases from vessel 32 leave through line 33 and pass through compressor 34 which increases the pressure of methane-rich gas product stream 35 to pipeline pressure. The stripped lean oil solvent leaves the bottom of vessel 32 as lean oil solvent in line 37 and is forced by pump 38 through line 14 for recycle to absorber 12.

If it is desired to utilize the process of this invention, as shown in FIG. 1, in a new installation without being combined with an existing lean oil absorber plant 10, the inlet $N_2$-containing gas stream is fed to line 13 through line 21 and the flashed solvent is diverted through line 44 to line 17 so that the process can operate without use of a distillation column, the lean oil solvent being regenerated solely by flashing. A plurality of flashing stages ending in a vacuum stage may be needed, however, depending upon the content of $C_5+$ hydrocarbons in inlet gas stream 21, in order to prevent buildup of $C_5+$ hydrocarbons.

Figure 3:
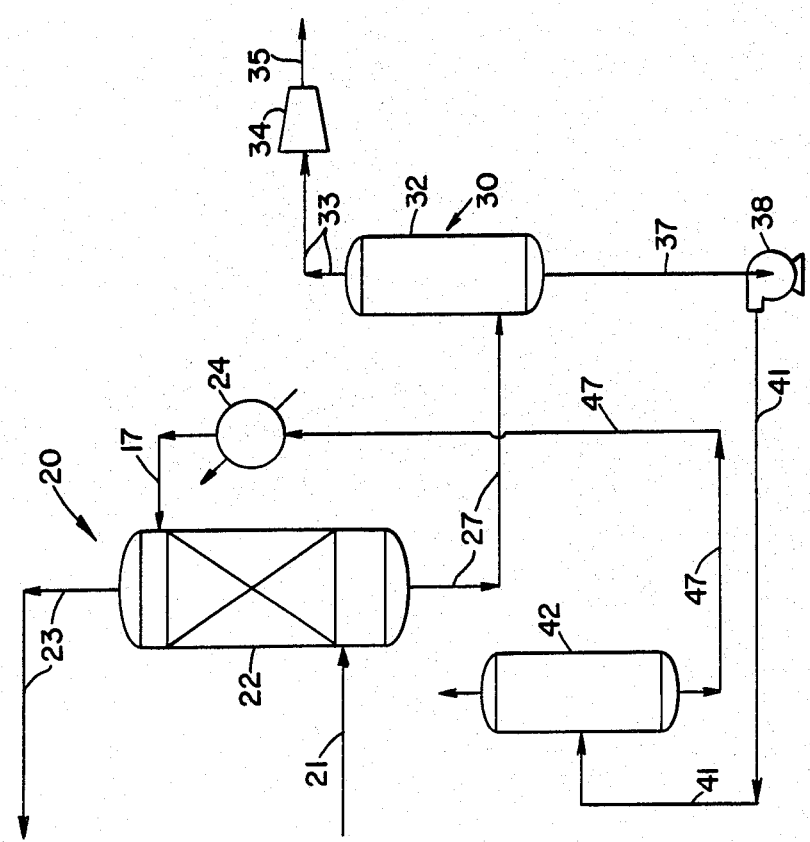
FIG. 3 is a schematic flow sheet which is exactly the same as FIG. 1 except that it includes the deleted dashed lines in FIG. 1 as solid lines.

Alternatively, however, a new still or distillation column 42 may be utilized, as shown in FIG. 3, by diverting the solvent through line 41 to still 42 and then, after regeneration, through line 47 and cooler 24 to join line 17.

Figure 2:
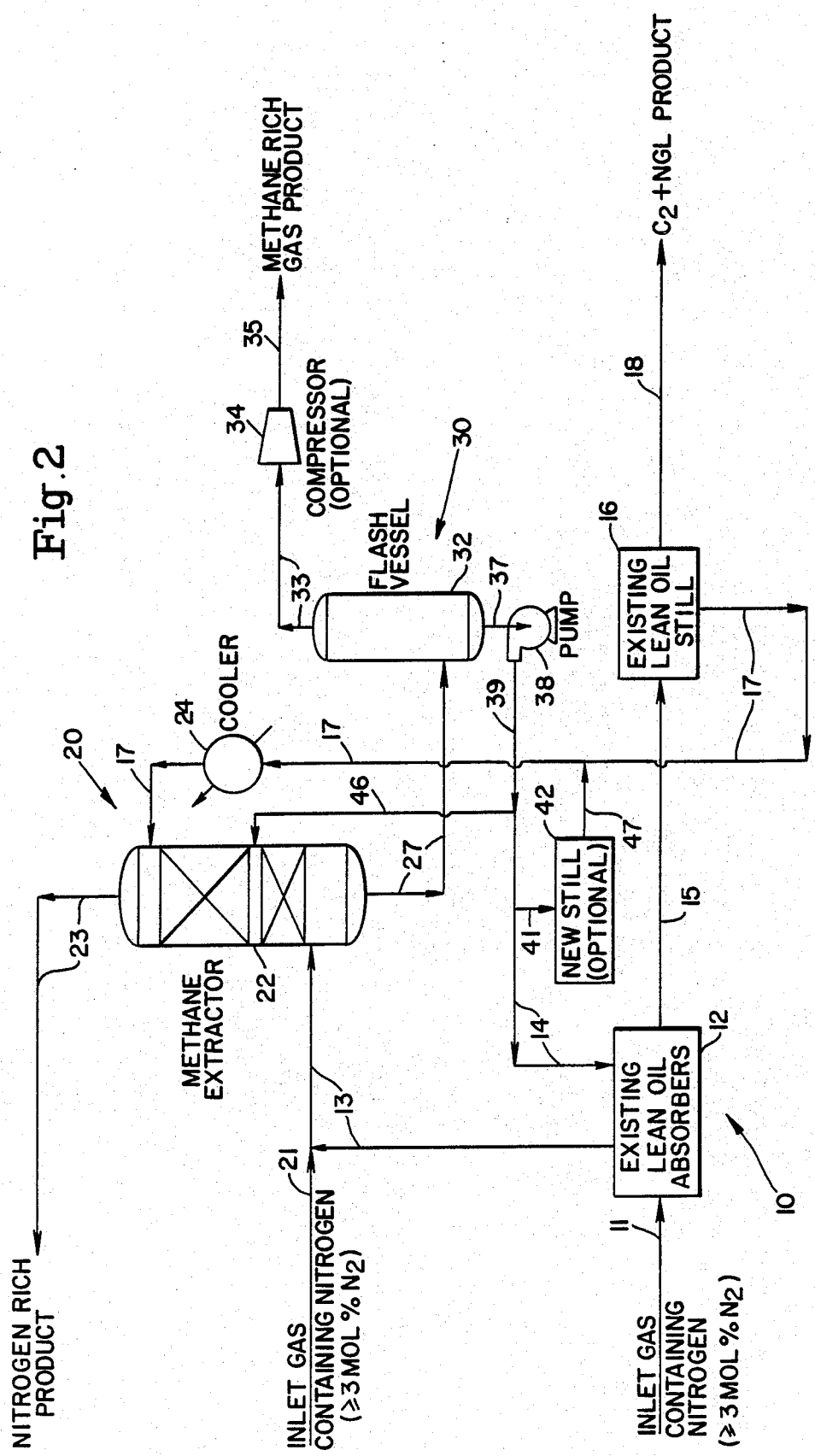
FIG. 2 is a schematic flow sheet which is exactly the same as FIG. 1 except that a portion of the flashed solvent is recycled to the middle of the methane extractor.
Figure 4:
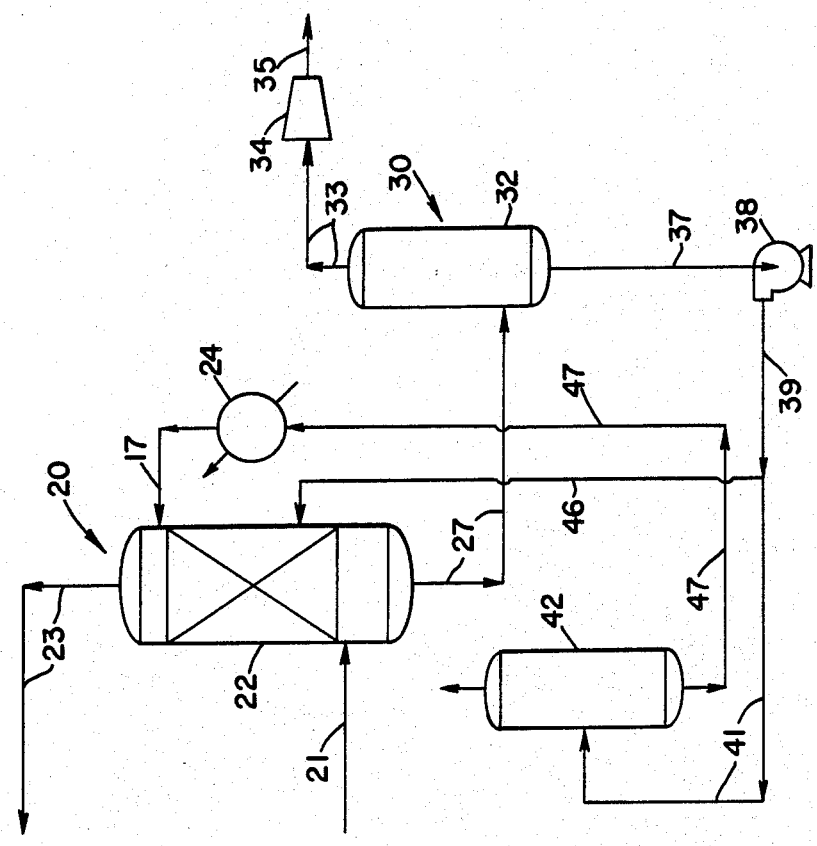
FIG. 4 is a schematic flow sheet which is exactly the same as FIG. 2 except that it includes the deleted dashed lines in FIG. 2 as solid lines.

The process shown schematically in FIG. 2 is exactly the same as in FIG. 1 except that a portion of the flashed solvent is recycled to the midsection of methane extractor 22. If the installation is to be a new one and not in combination with an existing absorber plant, it is also the same as FIG. 2 except that: (1) new still 42 is needed to provide very lean solvent to be fed to the top of column 22 through lines 47 and 17 and (2) new flashed solvent line 46 is also required to provide moderately lean solvent for the midsection of methane extractor 22. This moderately lean solvent is produced by flashing within Flash Vessel 32 and passes through line 37, pump, 38, line 39, and line 46 to enter, cooler 24, line 17 and extractor 22. This arrangement enables: (a) most of the methane to be absorbed in the upper section of extractor 22 by the very lean solvent from line 17 and (b) the $C_2+$ hydrocarbons to be absorbed in the mid-to-low sections of extractor 22 by (1) the slipstream of flashed solvent from line 46 and (2) the downflowing $C_1$-containing solvent from line 17.

The nitrogen-rich product leaving the top of extractor 22 through line 23 is at a pressure not far below its inlet pressure and can readily be compressed by a compressor and injected into the ground through suitable injection wells. Alternatively, if economically justifiable, the nitrogen stream can be passed through a gas expansion turbine for power recovery before venting to the atmosphere.

Because it will be readily apparent to those skilled in the art of treating hydrocarbon gases and hydrogen off-gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. A process for separating $C_1+$ hydrocarbons and nitrogen from a nitrogen-rich gas stream which contains more than 3 mol % of said nitrogen, comprising the following steps:
    A. contacting said nitrogen-rich gas stream with a lean oil, comprised of paraffinic, aromatic or cyclo hydrocarbons or mixtures thereof having molecular weights ranging between 75 and 250, at temperatures no lower than −40° F. to produce a nitrogen stream as an overhead product and a bottoms methane-rich oil stream; and B. flashing said bottoms methane-rich oil stream to recover a methane-rich overhead gas product and a lean oil rich bottoms stream; and recycling said lean oil stream to said contacting of step A.

2. The process of claim 1, wherein said nitrogen-rich gas stream is a natural gas and is selected from the group consisting of:
A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

3. The process of claim 2, wherein said contacting is at a pressure of 72.5–1,320 psia.

4. The process of claim 1, wherein said contacting is conducted in a methane extraction column, which includes a reboiler and is operable in extractive stripping mode.

5. The process of claim 1, wherein said flashing produces a bottoms stream which is split into a main oil stream, containing less than 15 mol % hydrocarbons, for recycling to said contacting and an oil slipstream which is regenerated to form said lean oil stream.

* * * * *